United States Patent [19]

Mullis

[11] Patent Number: 5,234,824
[45] Date of Patent: Aug. 10, 1993

[54] RAPID PURIFICATION OF DNA

[75] Inventor: Kary B. Mullis, La Jolla, Calif.

[73] Assignee: Specialty Laboratories, Inc., Calif.

[21] Appl. No.: 892,168

[22] Filed: Jun. 2, 1992

Related U.S. Application Data

[63] Continuation-in-part of Ser. No. 611,921, Nov. 13, 1990, Pat. No. 5,187,083.

[51] Int. Cl.$^5$ .................. C12P 19/34; C12N 1/08; C12N 1/06
[52] U.S. Cl. .................................. 435/91; 435/6; 435/259; 435/270; 435/803; 435/820; 536/23.1; 935/19; 935/20; 935/21
[58] Field of Search .................. 435/6, 91, 259, 270, 435/803, 820; 536/23.1; 935/19, 20, 21

[56] References Cited

U.S. PATENT DOCUMENTS 4,963,658 10/1990 Kung et al. .......................... 435/6
5,110,424 5/1992 Chin .................................. 204/180.1
5,187,083 2/1993 Mullis .................................. 435/91

OTHER PUBLICATIONS

*Lecture Course on the Polymerase Chain Reaction*, Chapter Entitled, "Rapid Purification of DNA From Blood," K. B. Mullis, Fundación Juan March, Serie Universitaria, No. 263, Oct. 1991.

*Primary Examiner*—Herbert J. Lilling
*Attorney, Agent, or Firm*—Harris F. Brotman

[57] ABSTRACT

The present invention provides a method for rapidly obtaining substantially pure DNA from a biological sample containing cells. The method involves gently lysing the membranes of the cells to yield a lysate containing genomic DNA in a high molecular weight form. The lysate is moved through a porous filter to selectively trap the high molecular weight DNA on the filter. The DNA is released from the filter using an aqueous solution to form a solution containing substantially purified DNA, from which the DNA may analyzed or recovered.

12 Claims, No Drawings

RAPID PURIFICATION OF DNA

This application is a continuation-in-part of application Ser. No. 07/611,921, filed Nov. 13, 1990, now U.S. Pat. No. 5,187,083 on behalf of the same inventor.

The present invention relates to a method for rapidly purifying DNA from cells and tissues and more particularly to a method for rapidly obtaining substantially purified DNA from whole blood.

BACKGROUND OF THE INVENTION

Purifying DNA from tissue or cell samples is complicated, time consuming, and often requires chemical and equipment that are hazardous and/or expensive. Most current methods for DNA preparation use traditional organic solvent extractions and/or absorption columns. In general, optimal recovery of DNA from biological samples is achieved by a phenol extraction followed by ethanol precipitation. This requires training and technical skills so that DNA is obtained substantially free of proteins and RNA.

Clinically useful applications of DNA purification from human tissues, for example, involve the detection of disease-causing, viral-specific genomes incorporated into human chromosomes, such as human immunodeficiency virus (HIV). Another useful application is the detection of disease causing genes, such as cystic fibrosis, sickle cell anemia, and Duchenne muscular dystrophy.

Kits are now available which allow DNA isolation from tissues without the use of phenol/chloroform extraction. For example, A.S.A.P.™ Genomic DNA Isolation Kit, Boehringer Mannheim Biochemicals, Indianapolis, Ind.; and The Extractor™, Molecular Biosystems, Inc., San Diego, Calif. These kits employ an ion exchange column to retain DNA on the basis of DNA's electrical charge. A disadvantage of these kits is that the entire procedure from cell lysis to elution of purified DNA requires two to four hours for most samples.

Known procedures for DNA purification from whole blood require cumbersome and time-consuming steps for cell lysate preparation. A typical method for preparing specimens of whole blood to purify DNA involves first purifying the mononuclear cells by banding in a density gradient such as ficoll hypaque (Pharmacia, Inc.) washing, then lysing the cells. The cell purification step is necessary because hemoglobin is reported to interfere with the PCR amplification. The isolated mononuclear cells are washed twice with phosphate buffered sales (PBS), then resuspended in 1 ml of PBS. A smear of the cell suspension is made and stained with Wright stain. The proportion of mononuclear cells is consistently found to be greater than 95%. A white cell count is then determined in a Coulter counter on an aliquot of each cell suspension. The cells are then pelleted and lysed by a quick lysis method to give a minimum cell concentration of $3 \times 10^6$ cells per ml. Proteinase K is added to a final concentration of 120 micrograms/ml and the lysates are incubated at 60° for 1 hour. The proteinase K is then inactivated by a 10-minute incubation at 95° C..

Mass screening of the human blood supply would require a mass scale-up of a traditional DNA purification method to detect viral-specific DNA. The cost would be very high for scaling up these methods to purify DNA obtained from either large numbers of samples or large sample volumes collected from a large portion of the population. Accordingly, it is desirable to have a method for rapidly, simply, and inexpensively obtaining purified DNA from small or large volumes or numbers of samples of donated human blood or other tissues.

Furthermore, it would be beneficial if such a simple procedure suitable for rapidly purifying DNA yielded the DNA substantially free of contaminants that can interfere with hybridization techniques or the polymerase chain reaction. Such contaminants include RNA, heparin, detergents, and large amounts of some proteins, like hemoglobin. it would be further desirable for this simple method to yield large amounts of DNA that can be examined for the presence of a single copy of a targeted sequence using the PCR.

Therefore, there is a need for a convenient and reliable technique for purifying large amounts of DNA from biological tissue or cell samples that requires less time than current techniques and does not require organic, hazardous, or expensive reagents. A technique is also needed which can be inexpensively and easily scaled up or down, does not require prior separation of cells from the sample, such as red blood cells, and that yields purified DNA that is substantially free of RNA, proteins, and other contaminants interfering with detection of specific DNA sequences by hybridization and amplification techniques, including polymerase chain reaction techniques.

SUMMARY

A method for obtaining substantially purified DNA from biological samples embodying features of the present invention satisfies these needs. The method provides for rapidly obtaining substantially pure DNA from a biological sample containing cells. While a preferred biological sample is whole blood, the method can be used for a variety of samples containing cells and tissues from mammalian, bacterial, yeast and plant sources.

The method comprises a first step of gently lysing the membranes of the cells in a blood sample. Gentle lysing releases the contents of the cells as a lysate containing DNA. An object of gently lysing is to avoid high shear forces on the DNA so as to yield a portion of the DNA having a sufficiently high molecular weight to be selectively trapped on a membrane filter. The lysate, which includes the cellular contents in solution, is then filtered to selectively trap the portion of DNA on the filter. The portion of DNA trapped on the filter is substantially free of the cellular contents.

After trapping the portion of DNA on the filter, the method of the present invention provides a further step for releasing the DNA from the filter using an aqueous solution to form a solution containing the DNA. The DNA released from the filter is analyzed or can be recovered in substantially purified form from the solution.

The filter includes a surface that reversibly and specifically initially retains the portion of DNA. The surface of the filter can be a porous substrate, which can typically be selected from at least one of the group of materials consisting of cellulose acetate, polyvinylidene and polycarbonate. The substrate can be a membrane filter. The pore size of the substrate can be from about 0.2 microns to about microns. A preferred filter comprises a membrane filter comprised of cellulose acetate having a pore size of about 0.45 microns.

The step of gently lysing involves contacting the cells in the blood sample with a detergent, typically sodium dodecyl sulfate, in sufficient concentration to rupture the membranes, including nuclear membranes, and release the contents of the cells as a lysate containing DNA, a portion of the DNA having a molecular weight sufficiently high to be selectively trapped on a membrane filter. The lysing solution comprises a viscosity-increasing agent to maintain a high-viscosity and reduce shear forces on the DNA. The invention provides for rendering the membranes of the cells more susceptible to detergent lysis of their membranes. Such rendering includes but is not restricted to treatment of the biological sample with a proteinase.

An object of the invention is to apply the method of the invention to the isolation and purification of DNA from any biological sample wherein the non-DNA components of the sample can be rendered into sufficiently small molecular aggregates so as to pass unobstructed through a porous filter capable of trapping DNA of sufficiently high molecular weight.

The step of gently lysing the cells includes allowing the lysate to stand for about 2 to about 50 minutes after which the present invention provides for the step of filtering the lysate through the filter so that the filter selectively traps the high molecular weight DNA contained in the lysate. The complete lysate or an aliquot thereof, including the cellular contents or debris in solution, is filtered through the membrane filter. Movement of the lysate through the filter can be facilitated by suction filtration or by centrifugation.

The present invention provides for releasing the trapped, purified DNA from the filter using an aqueous solution to form a substantially purified solution of the DNA. The DNA is released from the filter in a substantially purified form. The present invention contemplates releasing the DNA trapped on the filter by immersing the membrane filter in a sufficient amount of distilled water heated to about 100° C. See brief description of the drawings in parent application Ser. No. 07/611,921 filed Nov. 13, 1990, now U.S. Pat. No. 5,187,083 which illustrates the following.

FIG. 1 shows a photograph of an agarose gel illustrating the distribution of DNA in a lysate of human whole blood, the filtrate of the lysate, and eluates of the filter; FIG. 2 shows a similar photograph illustrating the DNA content of a lysate of whole human blood before and after filtration; and FIG. 3 shows a similar photograph illustrating a comparison of DNA contained in lysates, filtrates, and eluates of whole human blood to standard amounts of human genomic DNA.

DETAILED DESCRIPTION

In order that the invention herein described may be more fully understood, the following detailed description is set forth.

According to the present invention, a method is provided for rapidly obtaining substantially pure DNA from a biological sample in less than about 30 minutes. The method comprises the steps of (a) gently lysing the membranes of the cells in a biological sample to release the contents of the cells as a lysate containing DNA; a portion of the DNA has a sufficiently high molecular weight to be selectively trapped on a filter. The step of gently lysing includes allowing the lysate to stand from about two minutes to about fifty minutes. (b) filtering the lysate, including the cellular contents or debris in solution, through a porous filter to selectively trap the portion of DNA on the filter, the portion of DNA rendered substantially free of the cellular contents.

The method of the invention further comprises the steps of releasing the portion of purified DNA from the filter using substantially purified water at about 100° C. solution to form a substantially purified solution of DNA. A further step involves recovering the DNA in substantially purified form from the solution.

The method of the present invention comprises a first step of gently lysing the membranes of the cells in a biological sample to release the contents of the cells as a lysate containing DNA in a sufficiently high molecular weight form to be trapped on a membrane filter. Lysis herein is the physical disruption of the membranes of the cells, referring to the outer cell membrane and, when present, the nuclear membrane.

The invention contemplates the use of a chemical detergent agent, preferably sodium dodecyl sulfate, for gently lysing the membranes of the cells. The invention contemplates other detergent chemical agents, including but not restricted to Triton-X100 TM and NP-40 TM . for lysing the membranes of the cells.

The method employs a viscosity-increasing agent in the lysing buffer solution to maintain a high viscosity. The concentration of the viscosity-increasing agent in the lysis buffer is sufficient to increase the viscosity of the lysing solution so as to reduce shear forces, thereby inhibiting the shearing of DNA. Accordingly, the DNA is maintained at sufficiently high molecular weight for trapping on the membrane filter. A preferred viscosity increasing agent is polyvinyl alcohol (molecular weight of 70,000 daltons to 100,000 daltons) at a 2% w/v concentration in the lysis buffer. Other viscosity-increasing agents which may be used include other water soluble polymers such as carbohydrates, polypeptides, or synthetic organic polymers. For example, agarose, polyvinyl pyrolidine, or collagen may be used as viscosity-increasing agents in the method.

The inventor determined that without a viscosity-increasing agent, blood dilutions greater than 1 to 10 resulted in a solution from which DNA could not be filtered. Dilutions less than 1 to 10 were too viscous to filter at all. Accordingly, the use of polyvinyl alcohol in the lysis buffer allows greater dilution of the blood samples without severe shearing of DNA and more uniformity from sample to sample in spite of the differences in viscosity among different blood samples. The use of the viscosity-increasing agent provides the advantage of allowing separation of the level of dilution of the blood from the final viscosity.

The method of the invention concerns gently lysing the membranes of the cells in a biological sample by chemical means along with gentle swirling of the vessel in which lysis is carried out. Gentle lysis is defined herein as the avoidance of strong shear forces, such as those created by excessive pipetting, vortexing, or sonicating a solution containing DNA, such that the DNA is converted to low molecular weight fragments. Gentle lysis in the method of the present invention provides shear forces sufficiently mild to yield a cell lysate with the majority of the genomic DNA fragments having a molecular weight sufficiently high to be trapped on a membrane filter. The present method separates the high molecular weight DNA from the other cellular contents in solution in the lysate by filtering all or a portion of the lysate including the cellular contents in solution through a porous filter on which the DNA fragments having sufficiently high molecular weight are trapped.

The invention embodies lysing that is sufficiently gentle so as to produce a lysate containing a portion of DNA having a molecular weight that allows it to be selectively trapped on a porous filter when the lysate is filtered through the filter.

Biological samples contemplated by the method of the present invention can be derived from mammalian, plant, bacterial and yeast sources. The biological sample can be in the form of single cells or in the form of a tissue. Cells or tissue can be derived from in-vitro culture. Where the cells of the biological sample are less susceptible to gentle lysis, the method of the present invention contemplates rendering the cells more susceptible to detergent lysis. Rendering can be achieved by treating the biological sample with a proteolytic agent such as proteinase K as the cells are contacted with detergent (Ausubel, F. M., et al. eds., *Current Protocols in Molecular Biology*, p. 2.2.2., John Wiley & Sons (1987)). Cells which are less susceptible to detergent lysis include those with cell walls, that is, bacteria, yeast, and plant cells. Cells embedded in tissues can also be made more susceptible to gentle lysis by treating the tissue with proteinase K. ibid.

The step of gently lysing the membranes of the cells to release the contents of the cells as a lysate containing a portion of the DNA in high molecular weight form includes allowing the lysate to stand from about 2 minutes to about 50 minutes, during which time the lysate is formed. The invention provides for the step of filtering all or part of the lysate, including cellular contents, after the lysate has stood, through a porous filter to selectively trap the portion of high molecular weight DNA on the filter. The DNA trapped on the filter is substantially purified, that is, free of other cellular contents.

The filter provided by the present invention incorporates a surface that selectively and reversibly traps substantially all of the high molecular weight DNA in the lysate. The surface of the filter can be a porous substrate comprised of a material selected from at least one of the group consisting of cellulose acetate, polyvinylidene, or polycarbonate. The porous substrate is preferably cellulose acetate. A preferred form of the porous substrate is a membrane filter having a pore size from about 0.2 microns to about 0.8 microns. A most preferable filter is a membrane filter comprised of cellulose acetate having a pore size of about 0.45 microns.

According to the present invention, the lysate, including cellular contents, is filtered through the filter at a rate of about 0.025 ml/cm$^2$/minute to about 0.5 ml/cm$^2$/minute. The rate is preferably about 0.25 ml/cm$^2$/minute. The invention contemplates moving the lysate through the filter by suction filtration (see Examples 3-7) or by centrifugation (see Examples 1 and 2), but the invention is not limited to these two methods for moving the lysate through the filter.

Whole blood is a typical biological sample containing cells whose outer and nuclear membranes are gently lysed by the method of the present invention. The red blood cells in human blood are not nucleated and do not contain genomic DNA, but the white cells do contain nuclei with genomic DNA. In a typical protocol contemplated by the present invention, as described below in Example 3, whole blood was gently lysed by mixing, along with gentle swirling, a 100 microliter aliquot of whole blood with lysis buffer and incubating for 5-10 minutes. The filtrate of whole blood lysate contained substantially all of the hemoglobin and substantially all of the other cellular and noncellular proteins of the blood. All of the components of the lysate, with the exception of the high molecular weight DNA, were apparently not trapped by the filter device and moved through the filter into the filtrate. If components of the lysate (other than the high molecular weight DNA) were trapped by the filter, it was apparent that they were not released by the method provided by the invention for releasing the DNA from the filter. Furthermore, the eluate from the filter after release of the DNA was in a substantially purified form of DNA as indicated by O.D. 260/280. The purity of DNA obtained by this method can be established by the ratio of absorbance at 260 nm to the absorbance at 280 nm. For highly purified DNA, this ratio is about 1.8 (Ausubel, F. M., et al., eds, *Current Protocols in Molecular Biology*, p. 2.2.3, John Wiley & Sons, New York, 1987).

Although not wishing to be bound by the following theory, it is believed that high molecular weight DNA released by gentle lysis of cells is trapped on the porous filter by virtue of the fact that the DNA chains are considerably longer than the inter-pore distance on the surface of the filter such that separate regions of a single high molecular weight DNA chain may be simultaneously drawn into different pores, thus preventing complete passage of the molecule through either pore. Accordingly, the high molecular weight DNA molecule is effectively trapped on and/or in the filter.

The present invention embodies the step of releasing the purified, trapped DNA from the filter using an aqueous solution to form a solution containing the DNA. A most preferred method for releasing the high molecular weight DNA trapped on the filter involves contacting the filter with an eluent comprising substantially pure water (see Examples 6 and 9).

A less preferred aqueous solution for releasing the high molecular weight DNA from the filter to form a solution containing DNA comprises a sufficient concentration of divalent cations, having a concentration from about 1 mM to about 100 mM. The invention more preferably employs a solution comprising 10 mM magnesium for releasing the high molecular weight DNA. The method also contemplates heating the filter device containing the trapped DNA in the presence of an aqueous solution. As shown in Example 7, DNA release is more efficient at 60° than at room temperature.

Another method contemplated by the present invention for releasing the high molecular weight DNA trapped on the filter employs contacting the filter with microwave radiation in the presence of a 10 mM magnesium solution to form a solution containing substantially purified DNA, as illustrated in Example 7 below. However, it is difficult to control the level of irradiation delivered.

The most preferable methods for releasing the high molecular weight purified DNA trapped on the filter involves immersing the filter in an eluent which is heated to a about 100° C. As shown in Example 8, the washed filters can be removed to a buffer containing magnesium in a tightly closed tube which is placed in a boiling water bath. In that way, from 50% to 100% of the DNA originally present in the blood can be recovered in a highly purified form.

The optimal method for releasing the high molecular weight DNA trapped on the filter, as shown in Example 9, involves removing the washed filter to a solution of distilled water in a tightly closed tube which is placed in a boiling water bath. The distilled water is brought to a temperature of about 100° C. This yields a salt-free DNA solution.

Although not restricted to the following explanation, it is conjectured that high molecular weight DNA trapped in a porous membrane filter by the method of the present invention can be released by cleaving the DNA into shorter, less easily trapped fragments. Cleavage achieves release of the DNA from the filter device by converting the long chains of DNA into shorter pieces that either diffuse off the top of the filter into eluant buffer or can be drawn with eluant buffer through the porous filter into the eluate. Although not wishing to be bound by any theory, the restriction enzymatic release of the high molecular weight DNA trapped in the filter (see Example 7) is consistent with the hypothesis that the high molecular weight DNA is trapped physically on the filter. The trapped DNA extends outside of the filter. Breaking of bonds holding the DNA to the filter can be accomplished by DNA cleavage alone.

According to the present invention, a step is provided for recovering the DNA in a substantially purified form. The invention contemplates recovery methods that involve removal of either all of the eluate or aliquots of the eluate solution containing substantially purified DNA released from the filter device. Such aliquots, as illustrated in the Examples below, can be subjected to a variety of analytical and synthetic techniques, such as described in Ausubel, supra, or in *Molecular Cloning: A Laboratory Manual*, Cold Spring Harbor, (1982).

Examples of devices for using the method of the present invention include standard laboratory filter holders and filters furnished by companies such as Millipore, Inc., Biorad, Inc., MSI, Inc., and Whatman, Inc. The method of the invention can be conducted in filtration devices which facilitate the movement of solutions through filters by means including centrifugation, suction, pressure.

In order that the invention described herein may be more fully understood, the following examples are set forth. It should be understood that these examples are for illustrative purposes only are not to be construed as limiting the scope of this invention in any manner.

EXAMPLE 1

Capture and Elution of DNA from Whole Blood on Centrifuge Filters—Effect on Magnesium Capture Whole blood samples from human volunteers were collected into heparinized or EDTA containing tubes. 100-microliter aliquots were transferred to 1.7 ml Eppendorf tubes. 900 microliters of lysis buffer, SDS/1X in Dulbecco phosphate buffered saline (SDS/PBS) consisting of 138 mM NaCl, 8.1 mM $Na_2HPO^4$, 0.5 mM $MgCl_2$, 1.1 mM $KH_2PO_4$, and 2.7 mM KCl were added with gentle swirling. The resulting lysate was allowed to stand at room temperature for 5–10 minutes, after which 750 microliters of lysate, including cellular contents, were filtered or passed through a Costar Spin-X TM (Cambridge, Ma.) centrifuge filter unit having a 0.22 micron cellulose acetate membrane filter. This filter served to selectively trap the high molecular weight DNA and separate it from the lysate. Each filter was then washed twice with 750 microliters of an SDS/PBS solution. This was followed by two passes of 750 microliters of 50 mM Tris chloride at pH 7.4.

Elution

100 MICROLITERS OF 50 mM Tris chloride, pH 7.4, containing 10 mM MgCl, was then pipetted into each filter contained in a Costar filter unit and the units were gently rocked at 37° C. for 10 minutes. The tubes were centrifuged and the filtrate recovered for gel analysis of the DNA. A further aliquot of the elution buffer was added to the filters and after 20 minutes at room temperature the elution buffer was filtered through and analyzed.

Results

The DNA was quantitatively released by the lysis procedure and efficiently trapped on the filters as indicated by agarose gel electrophoresis (see FIG. 1). The top row of FIG. 1 shows that the DNA was released in solution and recovered in that solution from the filters by elution with a buffer containing magnesium. The lanes labeled "L" each contained an aliquot of lysate before the lysate was moved through the filter. The lanes labeled "1" each contained an aliquot of magnesium-containing elution buffer which was run through the filter through which the lysate was previously moved. The lanes labeled "2" each contained an aliquot of magnesium-containing buffer run through the filter subsequent to the previous run-through of magnesium-containing buffer.

The bottom row of the gel shows the removal of the DNA from the lysate by the filter as a result of moving the lysate through the filter. The bottom row further shows that the DNA selectively trapped on the filter was subsequently removed by passing magnesium-containing elution buffer through the filter containing the trapped DNA. The lanes labeled "L" contained an aliquot of lysate, the lanes labeled "F" contained an aliquot of the filtrate of the lysate moved through the filter; and the lanes labeled "1" and "2" contained aliquots of magnesium-containing buffer, as above.

Approximately 10% of the DNA trapped on the filter was released and recovered.

EXAMPLE 2

Distribution of DNA in Lysate Before and After Lysate Moved Through Filter and Treated with Various Washes The purpose of this example was to show the removal of high molecular weight DNA from the lysate by the filter. As in Example 1, above, heparinized, human whole blood was collected, gently lysed, and transferred to a centrifuge filter unit. The centrifuge filter unit served as the filter for retaining the high molecular weight DNA. The centrifuge unit was spun for three minutes in a bench top centrifuge so as to filter the lysate, including the cellular contents, through the filter device by centrifugation. The filter was then washed sequentially with 750 microliter of (a) lysis buffer, (b) 50 mM Tris hydrochloride at pH 7.4, (c) (b) plus 10 mM magnesium chloride, and (d) a second aliquot of (c).

10 microliter aliquots of each fraction were applied to an agarose gel and electrophoresed at 20 volts/cm for thirty minutes. DNA was detected with ethidium bromide staining and ultraviolet light as described by Ausubel, F. M., et al., eds. Current Protocols in Molecular Biology, p. 2.5.4, John Wiley & Sons, New York, 1987. The fractions applied were as follows:
 1. whole lysate 2. filtered lysate
3. lysis buffer wash
4. 50 mM Tris wash
5. first magnesium elution
6. second magnesium elution
7. 1/20th of (5)
8. repeat of (5)

FIG. 2 depicts the results of agarose gel electrophoresis of these samples. Lane 1 contained a 10 microliter aliquot of the whole lysate, the total volume of which was 1 milliliter. Lane 2 contained a 10 microliter aliquot of the whole lysate following movement through the filter device. Lane 3 contained a 10 microliter aliquot of the lysis buffer wash. Lane 4 had a 10 microliter aliquot of the Tris buffer wash. Lane 5 contained a 10 microliter aliquot of the first elution with the buffer containing magnesium. Lane 6 contained a 10 microliter aliquot of the second elution with the buffer containing magnesium. Lane 7 contained 0.5 microliters of the first elution containing magnesium buffer. Lane 8 is a duplicate of lane 5.

Approximately 5% of the DNA present in the whole lysate was recovered after the first magnesium elution. After the second magnesium elution, an additional 5% of the DNA in the whole lysate was recovered.

EXAMPLE 3

Trapping and Elution of DNA from Whole Blood in a Millipore ™ Filtration Apparatus.

The purpose of this example was to explore the convenience and effectiveness of larger diameter filters for rapidly purifying DNA using the method of the present invention. Ten ml of human whole blood was drawn into a heparinized tube. The blood was gently lysed by the addition and admixture by gentle swirling at room temperature of 90 ml of lysis buffer, 1% SDS in 1×Dulbecco phosphate buffered saline consisting of 138 mM NaCl. 8.1 mM Na$_2$HPO$_4$, 0.5 mM MgCl$_2$, 1.1 mM KH$_2$PO$_4$, and 2.7 mM KCl. At 5-10 minutes post lysis, a 5 ml aliquot of the lysed blood volume, including the cellular contents, was vacuum-filtered through a 0.45 micron cellulose acetate membrane filter, 2.5 cm diameter, MSI, Inc. (Westboro, Mass.). The membrane was then washed twice with 3 to 5 ml of the lysis buffer and then 3 to 5 ml of the wash buffer, 50 mM Tris-HCl, pH 7.4. These washing steps were done with squeeze bottles containing the aforementioned solutions and were not carefully controlled with respect to volume. However, care was taken to completely wash the filter device until the filter was colorless. Completeness in the Tris buffer wash, which was used to remove SDS, was judged by the absence of foaming in the filter well on application of the final aliquot of wash buffer. Two 3-5 ml washes were adequate to accomplish these ends.

The filters were removed from the vacuum manifold and placed into 1 ml aliquots of an elution buffer containing 80 mM Tris-HCl at pH 9.0, 20 mM ammonium sulfate, 10 mM magnesium chloride in the shallow well of CoStar ™ (Cambridge, Ma.) plastic cell culture dishes. The dishes were placed in a rotary shaker for several hours at 37° C., at which time they were discovered to have evaporated to dryness. After addition of 1 ml aliquots of water, the dishes were placed back into the shaker for 30 minutes and aliquots taken for analysis.

Results and Conclusions

Filtration times for movement of the lysate through the filter, Were less than one minutes. DNA recovered from cellulose acetate under all conditions was 100% as judged from agarose gel electrophoresis as shown in FIG. 3.

Lanes 1 and 2 contained aliquots of human DNA standards, each containing the equivalent of 10,000 copies of the human genome. These lanes served as a direct comparison to lanes 3 and 4, indicating that the release of DNA from the cells by the lysis buffer was complete. It should be noted in lanes 3 and 4 that the lysis buffer containing SDS interfered with the mobility of the DNA on the agarose gel. Lanes 50-10 consisted of aliquots containing DNA released from the filter device by the elution buffer. 100% efficiency for the entire process would be indicated by DNA bands that were five times brighter than the standards in lanes 1 and 2. The brightness of lanes 5-10 indicated DNA recoveries in the 50% to 100% range, recoveries considerably higher than the approximately 10% recoveries observed in FIGS. 1 or 2 (Examples 1 and 2) above.

EXAMPLE 4

Comparison of Nitrocellulose and Cellulose Acetate Filters

The purpose of this experiment was to compare the abilities of nitrocellulose and cellulose acetate filters to specifically and reversibly retain DNA released from recently lysed cells; and to determine if time elapsed between lysis and movement of lysate through a filter had a significant effect on filtration time or DNA recovery.

Ten ml of human whole blood was drawn into a heparinized tube. The blood was lysed by the addition at room temperature of 90 ml of lysis buffer. The lysis buffer was 1% SDS in 1×Dulbecco phosphate buffered saline consisting of 138 mM NaCl, 8.1 mM Na$_2$, 1.1 mM KH$_2$PO$_4$, and 2.7 mM KCl. At various times post-lysis, 5 ml aliquots of the lysed blood volume, including cellular contents, were vacuum filtered through either a 0.45 micron cellulose acetate membrane filter, 2.5 cm diameter, MSI, Inc., or a 0.45 micron nitrocellulose membrane filter, 2.5 cm diameter, Whatman Filters, (New Jersey). The membranes were then washed and treated as in Example 3, above, except that elution time was two hours at 42° C.

Results and Conclusions

As shown in Table 1 both nitrocellulose and cellulose acetate filters specifically and reversibly trapped high molecular weight DNA from lysed cells. The DNA trapped on the filter appeared to be purified, that is, substantially free of the cellular contents. Cellulose acetate filters, on average performed better than nitrocellulose filters as measured by yield and purity of recovered DNA.

TABLE 1

| | 2.5 CM Filter | Time | OD260/ OD280 | µg Recovered from 0.5 mL |
|---|---|---|---|---|
| 1. | CELLULOSE ACETATE | 2 | 1.88 | 12.9 |
| 2. | " | 10 | 1.76 | 14.0 |
| 3. | " | 20 | 1.87 | 21.8 |
| 4. | " | 30 | 1.79 | 12.5 |
| 5. | " | 40 | 1.81 | 17.6 |
| 6. | " | 50 | 1.79 | 15.8 |
| 7. | CELLULOSE NITRATE | 2 | 1.76 | 11.3 |
| 8. | " | 10 | 1.73 | 17.2 |
| 9. | " | 20 | 1.21 | IND* |
| 10. | " | 30 | 1.35 | 8.15 |

TABLE 1-continued

| 2.5 CM Filter | | Time | OD260/ OD280 | μg Recovered from 0.5 mL |
|---|---|---|---|---|
| 11. | " | 40 | 1.63 | 11.0 |
| 12. | " | 50 | 1.64 | 10.8 |

*Indeterminate

The purity of DNA obtained by this method can be established by the ratio of absorbance at 260 nm to the absorbance 15 280 nm. For highly purified DNA, this ratio is about 1.8 (Ausubel, F. M., et al., eds., *Current Protocols in Molecular Biology*, p. 2.2.3, John Wiley & Sons, New York 1987). A limitation of the Millipore Filtration apparatus used in this experiment was a tendency for the lysate to leak around the O-ring gaskets in the filter holder. This resulted in a minor amount of residual lysate on the edge of the filters when they were removed prior to elution of the trapped DNA. Subsequently, this material contaminated the DNA recovered by Elution. When the experiment was being analyzed by gel electrophoresis, this contamination source was inconsequential. When the DNA was subjected to spectral analysis, this contamination affected the measurements. When this problem was addressed by coating the O-rings with silicon grease prior to use, results, such as those presented in Table 1, were obtained. These results confirmed that the method of the invention generated highly purified DNA.

The time from lysis until movement of the lysate was through the filter device was varied from two minutes to 50 minutes. The time did not appear to affect the recovery of DNA, as shown in Table 1. It was observed that the time from lysis to filtration did not affect the time required to move the lysate through the filter, which in every case was less than one minute.

EXAMPLE 5

Rapid Recovery of DNA from Membrane Filters By Use of Microwave Radiation

The purpose of this example was to observe the effects of microwave radiation on the release of DNA trapped on the filter. Twelve Nucleopore TM 0 45 micron cellulose acetate/nitrate membranes, 2.5 cm in diameter, Nucleopore Corp., Pleasanton, Calif. 94566, were used to extract DNA from human blood lysates as described in Example 3.

After filtration and washing, the filters were placed in 1.7 ml Eppendorf type tubes with screw-on caps and rubber O-rings. 1 ml of the elution buffer (described in Example 3) was added to each.

The elution was performed by exposing the tubes to one minute of microwave radiation in a Kenmore Model No. 565 8738310 Microwave oven in the defrost setting. This was sufficient to heat the tubes to about 60° C. The tubes were subjected to a second minute in the microwave after a brief exposure to cool water. Ultraviolet absorbance measurements were made on the liquid remaining in the tubes and are shown in Table 2.

TABLE 2

| | 260 nM × 1000 | 280 nM × 1000 |
|---|---|---|
| 1. | 249 | 207 |
| 2. | 324 | 258 |
| 3. | 175 | 140 |
| 4. | 232 | 189 |
| 5. | 204 | 157 |
| 6. | 149 | 110 |
| 7. | 150 | 121 |
| 8. | 197 | 155 |
| 9. | 255 | 206 |
| 10. | 307 | 263 |
| 11. | lost tube | |
| 12. | 220 | 171 |

The average absorbance value of 0.219 at obtained at 260 nm corresponds to a recovery of DNA of about 64% based on normal blood values of 36 micrograms of DNA/ml of blood. The results in this Example indicate that a 1-minute exposure to microwave radiation can replace the more lengthy 2-hour procedure of Example 3. Use of the conditions of this Example significantly shorten the working time required to obtain substantially purified DNA using the method of the present invention.

EXAMPLE 6

ELUTION FROM CELLULOSE ACETATE FILTERS WITH VARIOUS SOLUTIONS

The purpose of this example was to determine the effects of various cationic solutions on the release of DNA trapped on filter by the method of the present invention. Filter membranes retaining trapped DNA were prepared as in Example 3. The filters were removed from the apparatus and each placed in a shallow well of a Costar TM plastic cell culture dish, and treated with one milliliter of elution buffer as described in Table 3. Elution was performed at 42° C. with gentle rocking on a thermostated rotary shaker for 15 minutes at which point the liquid was decanted and analyzed at 260 nM and 280 nM for the appearance of DNA.

The elution was continued by returning the liquid to the wells containing the filters and rocking for another six hours at 42° C. As in Example 3, the contents of the wells evaporated to dryness during this time. A milliliter of water was restored to each well and the dishes were placed back onto the shaker for 30 minutes just prior to analysis of the eluate. The results are presented in Table 3. Percent recovery, as shown in the right-hand column of Table 3 was based on the assumption of the presence of 5 million nucleated cells per milliliter of blood (36 micrograms DNA/ml) and 50 micrograms of DNA per OD260 unit.

TABLE 3

| Treatment Recovery | 15 Min. 42C Elution | | 6 Hours 42C Elution | | OD260/% OD280 | |
|---|---|---|---|---|---|---|
| | OD260 nM | OD280 nM | OD260 nM | OD280 nM | | |
| 1. Water | 0.58 | .041 | .069 | .101 | .683 | 19 |
| 2. 80 mM Tris 20 mM (NH4)2 (SO4)pH9 | .125 | .095 | .181 | .147 | 1.79 | 50 |
| 3. 2 + 1 mM MgCl2 | .068 | .046 | .191 | .145 | 1.32 | 53 |
| 4. 2 + 5 mM MgCl2 | .074 | .049 | .174 | .126 | 1.38 | 48 |
| 5. 2 + 10 mM MgCl2 | .169 | .120 | .282 | .204 | 1.38 | 78 |
| 6. 2 + 100 mM MgCl2 | .042 | .027 | .080 | .067 | 1.19 | 22 |
| 7. 2 + 10 mM ZnCl2 | No data | 50 1 prec. | .098 | .088 | 1.11 | 27 |
| 8. 2 + 5% EtOH | .121 | 0.84 | .255 | .198 | 1.28 | 70 |
| 9. 2 + 10 mM CaCl2 | .057 | .034 | .108 | .101 | 1.06 | 30 |

TABLE 3-continued

| Treatment Recovery | 15 Min. 42C Elution | | 6 Hours 42C Elution | | OD260/% OD280 | |
|---|---|---|---|---|---|---|
| | OD260 nM | OD280 nM | OD260 nM | OD280 nM | | |
| 10. 2 | .115 | .103 | .059 | .097 | 0.61 | 16 |
| 11. 2 + 10% EtOH | .074 | .052 | .111 | .083 | 1.33 | 30 |
| 12. 2 + 100 mM CaCl$_2$ | .062 | .041 | .121 | .092 | 1.31 | 33 |

These results indicated that of the 12 solutions tested, the solution containing 10 mM magnesium was preferred for the purpose of releasing and recovering the highest amount of DNA in a substantially purified form.

EXAMPLE 7

EFFECT OF RESTRICTION ENZYME

The purpose of this example was to determine the effects of restriction enzyme, heat, and microwave radiation on the release of DNA from the filter using the method of the present invention. Nucleopore ™ filter membranes retaining trapped DNA were prepared as in Example 5. The filters with the trapped DNA were placed in Eppendorf tubes. To each tube was added 1 ml of elution buffer. The buffer, pH 9.0, was 20 mM in ammonium sulfate, 80 mM in Tris-HCl, and 10 mM in magnesium chloride. The tubes were subjected to several elution protocols as described below, and the eluted DNA was detected by its optical absorbance. TaqI, a restriction endonuclease, was obtained from New England Biolabs, Beverly, Ma. The microwave radiation was generated at "defrost" setting by a Kenmore Microwave Oven, Model No. 56587383310 obtained from Sears, Los Angeles, Calif.

| Tubes | Protocol |
|---|---|
| 1,2 | Left at 60C with no additions for either 45 minutes or 90 minutes. |
| 3,4 | Left at 23C with no additions for either 45 minutes or 90 minutes. |
| 5,6 | Left at 60C with addition of 50 Units of TaqI for either 45 minutes or 90 minutes. |
| 7,8 | Microwaved at low power for 1 minutes, measured, then allowed to sit for 45 minutes, then microwaved at low power for 1 minutes. |

The results are shown in Table 4.

TABLE 4

| | 45 min | | 90 min | | | |
|---|---|---|---|---|---|---|
| | OD260 × 1000 | OD280 × 1000 | OD260 × 1000 | OD280 × 1000 | | |
| 1. | 141 | 097 | 162 | 106 | Microwaved 1 minute | |
| 2. | 158 | 118 | 183 | 133 | | |
| 3. | 053 | 041 | 117 | 082 | 213 | 152 |
| 4. | 103 | 094 | 193 | 161 | 258 | 202 |
| 5. | 168 | 130 | 213 | 158 | | |
| 6. | 226 | 179 | 272 | 218 | | |
| | Microwaved 1 minute | | Microwaved 2 × 1 minute | | | |
| 7. | 453 | 366 | 460 | 368 | | |
| 8. | 251 | 198 | 285 | 222 | | |

The optical absorbance at 260 nm and 280 nm due to the quantity of TaqI used in this experiment was negligible. The results indicated that the concentration of restriction endonuclease used in this Example released some DNA trapped on the filter. However, the release of DNA was not as rapid as the release due to microwave radiation.

The results indicated that the release and recovery of DNA from these filters was enhanced by exposing to microwave radiation the filters retaining the trapped DNA in the presence of elution buffer containing magnesium.

EXAMPLE 8

EFFECTS OF VISCOSITY INCREASING AGENT AND TEMPERATURE OF ABOUT 100° C.

One-ml aliquots of remnant blood samples from a clinical laboratory were drawn into EDTA as an anticoagulant. The samples were placed into standard-sized scintillation vials and gently mixed by inverting several times with 20 ml of a lysis buffer of the following composition, which included the viscosity-increasing agent polyvinyl alcohol.

| | |
|---|---|
| Sodium chloride | 138 mM |
| Disodium hydrogen phosphate | 8 mM |
| Potassium dihydrogen phosphate | 1 mM |
| Magnesium chloride | 0.5 mM |
| Potassium chloride | 2.7 mM |
| Sodium dodecyl sulfate | 35 mM |
| Polyvinyl alcohol 30-70K MW | 2% W/V |

The lysis mixtures were allowed to stand at room temperature for 10 minutes after which the lysates, including the cellular contents, were filtered using suction through 2.5 cm diameter 0.45 micron cellulose acetate filters (MSI, Inc., Cat. No. E04WPO). The filters were held in a Millipore 12-position filtration device. The filters were washed until white by applying several milliliters from a squeeze bottle of the lysis solution above less the polyvinyl alcohol. The exact volume of the wash was not critical. The purpose of the wash was to remove all residual blood components except for the DNA, which was trapped on the filter.

A wash of either 50 mM Tris hydrochloride at pH 8 or a water wash was performed as above from a squeeze bottle. The purpose of this wash was to remove residual sodium dodecyl sulfate. This was accomplished with two or three 3–5 ml aliquots, the last of which would no longer generate foam. As before, the exact volume was not critical.

The filters were removed from the filtration apparatus into plastic, screw-cap conical tubes, 1.7 ml. One ml of a buffer composed of 50 mM Tris hydrochloride at pH 8 and 10 mM magnesium chloride was added to each tube so as to cover the filter, and the tubes were placed in boiling water for 15 minutes. The DNA was released from the filters into the liquid.

The tubes were briefly centrifuged to settle any cellulosic debris and the buffer was transferred to another tube. Optical density measurements at 260 nm and 280 nm were made on a portion of this buffer from which DNA concentrations were inferred using a standard conversion of 35 micrograms DNA/ml/OD unit. Another aliquot was subjected to a standard fluorometric assay for DNA (Vytasek, R., A sensitive Assay for the Determination of DNA, *Analytical Biochemistry* 120:243 (1982)). Correlation between the two methods is indicated in Table 5.

TABLE 5

Filter extraction of DNA from 1 mL whole blood

| Sample | OD260 | OD280 | 260/280 | ug/mL (OD)* | ug/mL (DABA) |
|---|---|---|---|---|---|
| 1 | 0.99 | 0.54 | 1.83 | 34.7 | 25.7 |
| 2 | 0.65 | 0.356 | 1.83 | 22.8 | 13.5 |
| 3 | 0.798 | 0.436 | 1.83 | 27.9 | 27.3 |
| 4 | 1.218 | 0.668 | 1.82 | 42.6 | 36.8 |
| 5 | 0.401 | 0.256 | 1.57 | 14 | 20 |
| 6 | 0.552 | 0.315 | 1.75 | 19.3 | 14.3 |
| 7 | 0.218 | 0.132 | 1.65 | 7.6 | 13.8 |
| 8 | 0.52 | 0.283 | 1.84 | 18.2 | 15.9 |
| 9 | 0.604 | 0.337 | 1.79 | 21.1 | 19.7 |
| 10 | 0.086 | 0.064 | 1.34 | 3 | 7.3 |
| 11 | 0.289 | 0.172 | 1.68 | 10.1 | 7.4 |
| 12 | 0.616 | 0.368 | 1.92 | 21.6 | 12.7 |
| 13 | 0.482 | 0.321 | 1.5 | 16.9 | 7.2 |
| 14 | 0.404 | 0.248 | 1.62 | 14.1 | 8.5 |
| 15 | 0.238 | 0.163 | 1.46 | 8.3 | 4.9 |
| 16 | 0.172 | 0.13 | 1.32 | 6 | 3.4 |
| 17 | 0.162 | 0.103 | 1.57 | 5.7 | 5.2 |
| 18 | 0.525 | 0.293 | 1.79 | 18.4 | 16.1 |
| 19 | 0.527 | 0.285 | 1.85 | 18.4 | 16 |
| 20 | 0.425 | 0.25 | 1.7 | 14.9 | 10 |
| 21 | 0.955 | 0.495 | 1.94 | 33.4 | 27.5 |
| 22 | 0.858 | 0.453 | 1.89 | 30 | 25.4 |
| 23 | 0.73 | 0.395 | 1.85 | 25.6 | 23.2 |
| 24 | 0.847 | 0.444 | 1.91 | 29.6 | 24.5 |
| 25 | 1.699 | 0.935 | 1.83 | 59.5 | 62.6 |
| 26 | 1.014 | 0.538 | 1.88 | 35.5 | 34 |
| 27 | 0.797 | 0.42 | 1.9 | 27.9 | 26.5 |
| 28 | 1.207 | 0.637 | 1.89 | 42.2 | 54.1 |
| 29 | 1.005 | 0.532 | 1.89 | 35.2 | 34.9 |
| 30 | 0.61 | 0.344 | 1.77 | 21.4 | 20 |
| 31 | 0.945 | 0.511 | 1.85 | 33.1 | 27 |
| 32 | 0.776 | 0.415 | 1.87 | 27.2 | 24.5 |
| 33 | 0.885 | 0.545 | 1.62 | 31 | 26.4 |
| 34 | 0.313 | 0.204 | 1.53 | 11 | 12 |
| 35 | 0.533 | 0.306 | 1.74 | 18.7 | 20.6 |
| 36 | 0.526 | 0.301 | 1.75 | 18.4 | 18.3 |
| 37 | 0.503 | 0.285 | 1.76 | 17.6 | 19.4 |
| 38 | 0.35 | 0.197 | 1.78 | 12.3 | 15.8 |
| 39 | 1.239 | 0.696 | 1.78 | 43.4 | 36.5 |
| 40 | 0.915 | 0.491 | 1.86 | 32 | 33.2 |

Average ug/mL DNA at 35 ug ssDNA/OD260 23.265
Average ug/mL by DABA DNA assay 21.3025
*DNA concentration based on 1 OD260 = 35 ug/mL

EXAMPLE 9

EFFECT OF DISTILLED WATER AND 100° C.

The procedure in Example 8 above, except for a change in the elution buffer, was applied to eleven aliquots of blood and a water blank control (Sample No. 10 in Table 6, below). The elution was performed as in Example 8 except that 1 ml of distilled water was substituted for the Tris and magnesium buffer. This had the distinct advantage of yielding DNA released from the membrane filter free of salts.

The eluted DNA was subjected to spectrometric examination as tabulated below, and the concentration of DNA calculated by assuming that an optical density at 260 nM of 1.0 indicates 35 micrograms DNA/ml. Ratios very close to 2.0 indicate a very high purity of single stranded DNA.

TABLE 6

| | OD260 mM | OD260/OD280 | uG DNA/ml |
|---|---|---|---|
| 1 | .762 | 1.98 | 24.6 |
| 2 | .796 | 1.95 | 27.9 |
| 3 | .740 | 1.99 | 25.9 |
| 4 | .890 | 2.01 | 31.1 |
| 5 | .905 | 2.01 | 31.6 |
| 6 | .910 | 1.98 | 31.8 |
| 7 | .949 | 1.93 | 33.1 |
| 8 | .881 | 2.00 | 30.8 |
| 9 | .930 | 2.00 | 32.5 |

TABLE 6-continued

| | OD260 mM | OD260/OD280 | uG DNA/ml |
|---|---|---|---|
| 10 | .057 | 1.50 | 2.0 |
| 11 | .891 | 1.99 | 31.1 |
| 12 | .883 | 1.98 | 30.9 |

Although the present invention has been described in considerable detail with regard to certain preferred versions, other versions are possible. For example, release of DNA trapped on the filter can be achieved by various treatments that are capable of cleaving long DNA chains. Such treatments might include freezing and thawing the filter retaining trapped DNA in eluting buffer. The filter with trapped DNA can be subjected to high temperatures achieved by any means. Any number of DNA-cleaving enzymes, including known restriction enzymes, can be used in the method of the present invention to release DNA trapped on the filter. Alternatively, the DNA trapped on the filter can be released by application of an electric field, such as in electroelution of DNA molecules from agarose gels.

Other specific uses for the method of the present invention include combining the method of the present invention with polymerase chain reaction amplification of DNA sequences trapped, recovered or otherwise purified by the present method. DNA trapped and purified on the filter of the present invention can lend itself to other analytical procedures, including microscopic analysis by conventional or scanning probe microscopes. Various devices containing porous filters known in the art may be used.

It should be understood that any biological sample containing DNA in high molecular weight form is subject to the method of the present invention. The method of the present invention is applicable to the isolation and purification of DNA from any biological sample wherein the non-DNA components of the sample can be rendered to sufficiently small molecular aggregates so as to pass unobstructed through a porous filter capable of trapping the high molecular weight DNA. Such samples includes stools, sputum, sperm and the like.

Further, the method of the present invention can be used to separate genomic from non-genomic nucleic acid sequences, including RNA sequences.

The method of the present invention can be adapted for large scale DNA purification from large volumes of lysate from blood, other cells, and tissues. For example, such scale up can be achieved by employing larger filters.

It is apparent that many modifications and variations of this invention as set forth above may be made without departing from the spirit and scope. The specific embodiments described are given by way of example only, and the invention is limited only by the terms of the appended claims.

What is claimed is:

1. A method for rapidly obtaining substantially pure DNA from blood cells comprising the steps of:
    (a) avoiding high shear forces by gently lysing the membranes of said cells for about from two to about fifty minutes with a solution comprising a detergent and a viscosity-increasing agent to release the contents of the cells as a lysate containing DNA, a portion of said DNA having a molecular weight sufficiently large to be selectively trapped on a membrane filter; and (b) filtering said lysate through a membrane filter to selectively trap said portion of DNA on the filter, wherein said filter comprises a porous substrate having a surface that reversibly and specifically traps said portion of DNA, said filter having a pore size from about 0.2 microns to about 0.8 microns.

2. The method of claim 1 further comprising the steps of:

(a) releasing said portion of DNA from said filter wherein said step of releasing comprises immersing said membrane filter for a period of from about 5 minutes to about 15 minutes in a solution of substantially pure water at a temperature of about 100° C. to release said portion of DNA trapped on said membrane filter into said solution to form a substantially purified solution of DNA; and (b) analyzing said substantially purified solution of DNA.

3. The method of claim 2 further comprising recovering said portion of DNA in a substantially purified form from said solution of distilled water.

4. The method of claim 2 wherein said solution of substantially purified water further comprises divalent cations selected from the group consisting of magnesium and calcium, wherein the cation concentration is less than about 100 mM.

5. The method of claim 1 wherein said viscosity-increasing agent is selected from at least one of the group consisting of water soluble polymers, sugars, polypeptides, and gelatin.

6. The method of claim 1 wherein said viscosity-increasing agent is polyvinyl alcohol.

7. The method of claim 1 wherein said lysate is allowed to stand from about 5 minutes to about 10 minutes.

8. The method of claim 1 wherein the filter is comprised of a material selected from at least one of the group consisting of cellulose acetate, polyvinylidene, and polycarbonate.

9. The method of claim 1 wherein the filter comprises cellulose acetate having a pore size of 0.45 microns.

10. The method of claim 1 wherein the detergent is sodium dodecyl sulfate.

11. The method of claim 4 wherein said cation concentration is about 10 mM.

12. The method of claim 1 wherein the step of lysing is performed at a temperature from about 0° C. to about 50° C.

* * * * *